United States Patent
Muraco et al.

(10) Patent No.: US 10,019,916 B2
(45) Date of Patent: Jul. 10, 2018

(54) DECORATIVE ELEMENT FOR MEDICAL DEVICES

(71) Applicants: Jessica Muraco, Brighton, MI (US); Sean M Diamond, Dover Plains, NY (US)

(72) Inventors: Jessica Muraco, Brighton, MI (US); Sean M Diamond, Dover Plains, NY (US)

(73) Assignee: Jessica Muraco, Brighton, MI (US)

(*) Notice: Subject to any disclaimer, the term of this patent is extended or adjusted under 35 U.S.C. 154(b) by 0 days.

(21) Appl. No.: 14/519,093

(22) Filed: Oct. 20, 2014

(65) Prior Publication Data

US 2015/0038877 A1    Feb. 5, 2015

Related U.S. Application Data

(63) Continuation of application No. 13/582,323, filed as application No. PCT/US2011/026820 on Mar. 2, 2011, now Pat. No. 8,863,415.

(60) Provisional application No. 61/309,567, filed on Mar. 2, 2010.

(51) Int. Cl.
   *G09F 3/20* (2006.01)
   *A61B 7/02* (2006.01)
   *B44F 99/00* (2013.01)

(52) U.S. Cl.
   CPC .............. *G09F 3/205* (2013.01); *A61B 7/02* (2013.01); *B44F 99/00* (2013.01); *Y10T 24/39* (2015.01); *Y10T 428/24008* (2015.01)

(58) Field of Classification Search
   CPC .................................. G09F 3/205; A61B 7/02
   See application file for complete search history.

(56) References Cited

U.S. PATENT DOCUMENTS

| | | | |
|---|---|---|---|
| 1,703,609 A * | 2/1929 | Gastrow et al. | 40/316 |
| 4,497,124 A * | 2/1985 | Olive | 40/299.01 |
| 4,802,550 A * | 2/1989 | Poore | 181/131 |
| 5,275,282 A * | 1/1994 | Ross et al. | 206/389 |
| D354,086 S * | 1/1995 | Rashman | D20/22 |
| 5,468,022 A | 11/1995 | Linder et al. | |
| D381,367 S * | 7/1997 | Rashman | D20/22 |
| 7,194,829 B2 | 3/2007 | Boire et al. | |
| 7,322,135 B2 | 1/2008 | Gulati | |
| D567,372 S * | 4/2008 | Chesnin | D24/128 |
| 2002/0032102 A1* | 3/2002 | Boire et al. | 482/11 |
| 2003/0221903 A1* | 12/2003 | Roby et al. | 181/131 |
| 2004/0249298 A1* | 12/2004 | Selevan | 600/528 |
| 2007/0241149 A1 | 10/2007 | Bhavnani | |
| 2008/0189995 A1 | 8/2008 | Boire | |
| 2009/0277055 A1* | 11/2009 | Madrigal et al. | 40/316 |

FOREIGN PATENT DOCUMENTS

WO    WO9010284    9/1990

* cited by examiner

*Primary Examiner* — Gary C Hoge
(74) *Attorney, Agent, or Firm* — Young Basile Hanlon & MacFarlane, P.C.

(57) ABSTRACT

A decorative device for use with a medical instrument having a tubing structure, the decorative device including at least one connector configured to removably couple to the tubing structure on the medical instrument, the connector having a face plate engaging structure configured to attachably engage at least tone decorative face plate member.

8 Claims, 2 Drawing Sheets

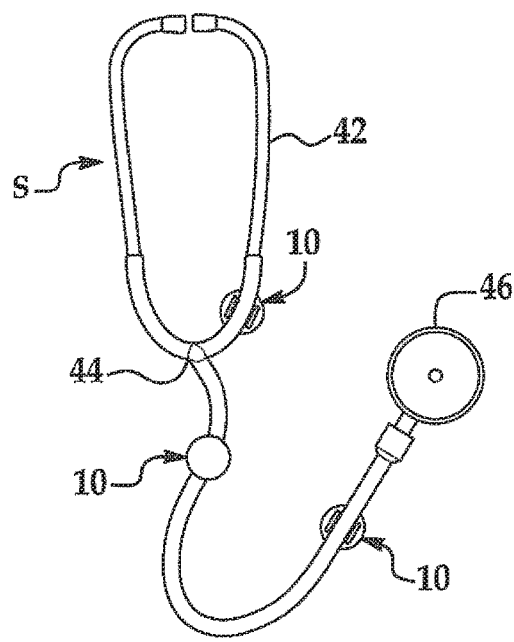
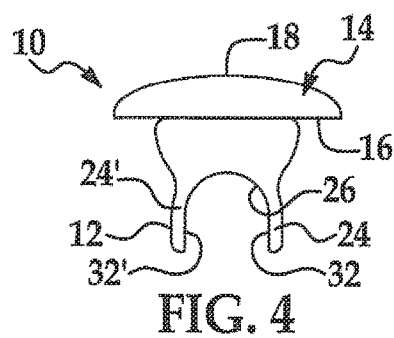
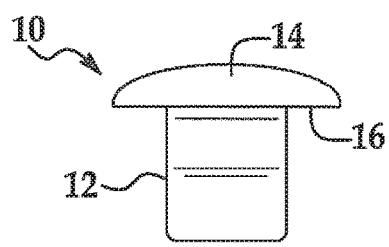
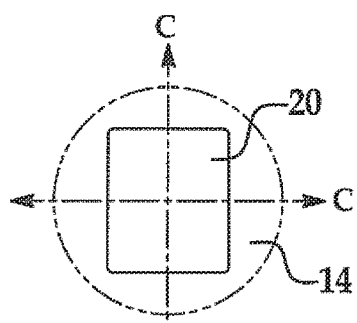
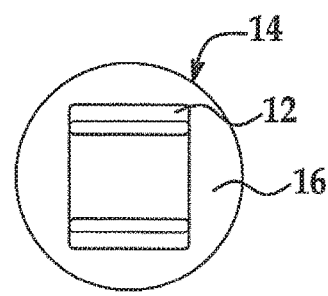
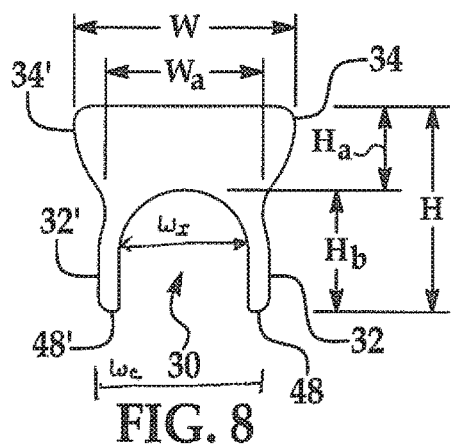
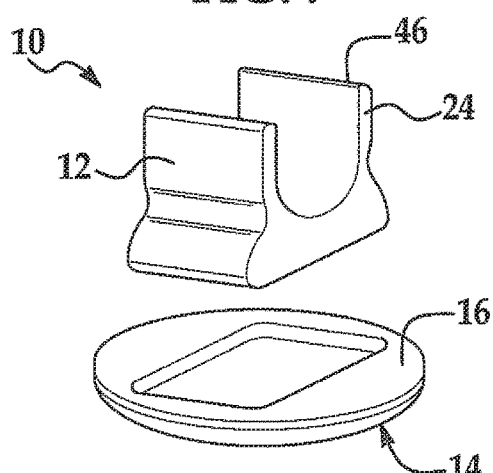

DECORATIVE ELEMENT FOR MEDICAL DEVICES

CROSS-REFERENCE TO RELATED APPLICATIONS

The following application is a continuation of U.S. application Ser. No. 13/582,323, filed on Nov. 26, 2012, which is a United States national stage application of International Patent Application No. PCT/US2011/026820, filed on Mar. 2, 2011, which claims the benefit of U.S. Application No. 61/309,567, filed on Mar. 2, 2010, each incorporated herein in its entirety.

BACKGROUND

The present invention pertains generally to the field of medical instruments.

Medical instruments such as stethoscopes and the like are important tools in patient diagnosis and care. Typically devices like stethoscopes are assigned to or even purchased by an individual health care professional. Alternately, in certain situations, various medical instruments such as stethoscopes and the like are assigned to an individual or associated with a given area such as a specific examination room treatment location or the like.

Regardless of the manner of purchase or acquisition, the various medical instruments need to be identified with owner and/or location. All too often similar looking devices such as stethoscopes and the like can be mislaid and confused. Thus it would be desirable to provide a device that can be integrated with a medical instrument such as a stethoscope to identify ownership and/or assigned location.

In order to provide effective medical care, various medical practitioners, including but not limited to physicians, nurses, medical assistants and various paramedical practitioners, routinely utilize medical devices such as stethoscopes. In order to provide personalized, effective medical care, great efforts have been made to reduce the institutional nature of such care. Medical garments of cheerful print and/or color are available. Given the nature of medical care and the need for cleanliness and freedom of movement, it is difficult for practitioners to individualize their garments or indulge in jewelry or other adornment. Thus the desire for suitable decorative items that can be worn or displayed by medical professionals has been largely overlooked or unmet.

SUMMARY

Disclosed herein is a device for use with a medical instrument having a tubing structure. The device includes at least one connector configured to removably couple to the tubing structure of a medical device and at least one decorative face plate member attached to the connector. The face plate member has at least one attachment region where it is connected to the connector and at least one decorative surface.

The device can be attached in an essentially immoveable fashion to a tubing structure associated with a medical instrument such as the stethoscope to personalize and/or identify the associated medical instrument. The device can be equipped with a suitable tracking mechanism such as an RFID mechanism so as to locate the associated medical instrument when lost or misplaced and/or pinpoint the location of the individual using the device within a treatment center.

It is also contemplated that the medical instrument can be equipped with multiple devices in order to further personalize or decorate the medical instrument.

DESCRIPTION OF THE DRAWING

The present invention is described in the following detailed description. In order to further disclose and describe the invention, reference is made to the following drawing figures in which like reference numerals are used where appropriate to describe the various elements throughout the various drawing figures. It is to be understood that the various drawing figures are illustrative rather than limitative of the present invention.

FIG. 3 is a front view of a stethoscope according to an embodiment of the invention disclosed herein;

FIG. 4 is a side view of the connector device of FIG. 1;

FIG. 5 is a lateral view of the connector of FIG. 1;

FIG. 6 is a top view of the connector of FIG. 1;

FIG. 7 is a bottom view of the connector of FIG. 1;

FIG. 8 is a detail plan view of the connector of FIG. 1; and

FIG. 9 is a bottom perspective view of the device of FIG. 1 with an alternate face plate member embodiment.

DETAILED DESCRIPTION

Figure 1:
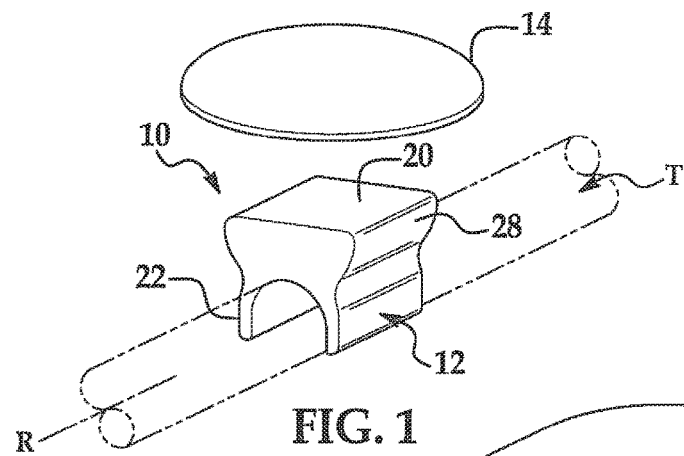
FIG. 1 is a perspective view of an embodiment of the invention disclosed herein.

Disclosed herein is a device for use with a medical instrument having at least one tubing structure. The device can be used to identify, decorate, or personalize the associated medical instrument. Suitable medical instruments having a tubing structure can include stethoscopes.

A device 10 disclosed herein includes a connector 12 configured to removably couple to a tubing structure T associated with the medical instrument. The device 10 also includes a face plate member 14 attached to the connector 12. The face plate member 14 has a connection surface 16 configured to engage the connector 12 and at least one decorative surface 18 oriented in a generally outwardly facing direction from the connector 12 and the associated with tubing T. In the embodiment depicted in FIG. 1, the face plate member 14 is a disc-shaped element having an essentially flat connection surface 16 on an opposed convex decorative surface 18 extending over the entire outwardly-facing surface of the face plate member 14. The decorative surface 18 may have other suitable configurations as desired or required. Non-limiting examples of such configurations can include various molded or engraved images or designs. The decorative surface 18 can include suitable printed indicia integrated into the face plate member 14 by any suitable process including molding, printing, lithography, and the like.

In the embodiment depicted in FIG. 1, the decorative face plate member 14 has an essentially planar connection surface 16. The decorative face plate member 14 is dimensioned to project beyond the boundaries defined by the corresponding perimeter connector 12. It is within the purview of this disclosure that, in certain embodiments, at least a portion of the outer edge of the face plate member 14 to be equal to or correspond with the perimeter defined by the connector 12. It is also contemplated that the decorative face plate member 14 can have one or more curved surfaces proximate to the planar connection surface 16 that permits the associated decorative face plate member 14 to cover or overlay at least a portion of one or more sides of the associated connector 12.

The decorative surface 18 can have any suitable configuration such as the non-limiting example contained in the embodiment depicted in FIGS. 4 and 5. The decorative surface 18 can have any suitable configuration. Thus, the decorative surface 18 can be planar, contoured, engraved, etc. The perimeter of the decorative face plate member 14 can have any aesthetically suitable geometry of which squares, ovals, and irregular outlines are non-limiting examples. In certain configurations, the connector surface 16 and the face plate member 14 can be configured with a suitable cavity or opening 38 (see FIG. 9) to matingly receive the connector 12 proximate to a face plate member engaging surface 20.

The face plate member 14 can be attached to the connector 12 by any suitable mechanical or chemical means including, but not limited to, adhesives, snap-fit mechanisms, and the like. In the embodiment depicted, it is contemplated that the respective connectors 12, 12' and the face plate members 14, 14' can be interchangeable; i.e., the connectors 12, 12' can receive various face plate members 14, 14' as desired or required. In the embodiment depicted in FIG. 1, attachment is accomplished by suitable, removable or permanent bond forming agents such as adhesives. In the embodiment depicted in FIG. 9, attachment can be accomplished by suitable mechanical means including snap fit, interference fit, or the like, employed alone or in combination with suitable adhesives. It is also within the purview of the present disclosure that the face plate member 14 can be integrally formed or permanently bonded in certain instances.

While the decorative face plate member 14 is depicted as resting on and generally outward from the connector 12, in certain embodiments the decorative face plate member 14 can be contoured to overly additional sides or regions of the connector 12 to provide decorative ornamentation overlaying one or more side regions of the connector 12. It is also contemplated that the connector surface 16 of the decorative face plate member 14 can be configured with a suitable engagement member, contoured to matingly and lockingly engage with a suitable member configured on the connector 12.

Figure 2:
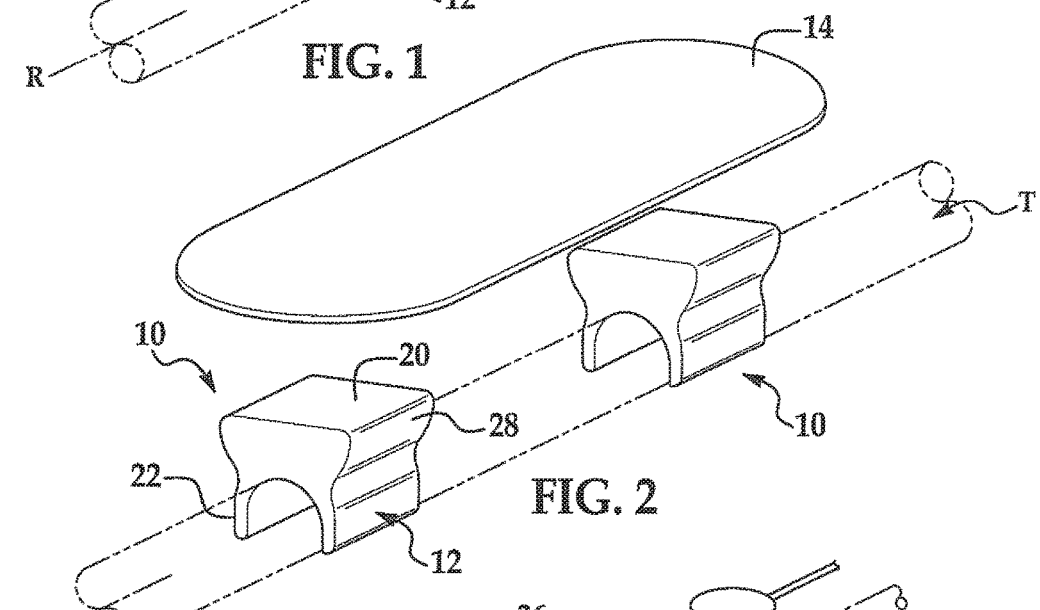
FIG. 2 is a perspective view of an alternative embodiment of the invention as disclosed herein.

In the embodiment depicted in FIG. 1, the decorative face plate member 14 is connected to one connector 12. The decorative face plate member 14' can be connected to more than one connector 12, such as connectors 12, 12', in the manner depicted in FIG. 2. Where two or more connectors 12, 12' are utilized, it is also contemplated that individual decorative face plate members 14, 14' can be configured to link or interlock as desired or required (for example, see FIG. 2A, FIG. 2B, and the like.

The connector 12 includes the suitable face plate member engaging surface 20. The face plate member engaging surface 20 can have any suitable contour configured to effectively engage the associated face plate member 14. In the various embodiments depicted in the drawing figures, the face plate member engaging surface 20 of the connector 12 is a generally rectangular planar surface. Other side dimensions are contemplated. Where the associated face plate member 14 is configured with a suitable connector engaging member, the face plate member engaging surface 20 can be configured with a suitable mating engagement region.

In the embodiment depicted in the various drawing figures, the face plate member engaging surface 20 has a rectilinear dimension in which the four sides are either equal or in which the surface 20 is rectangular. In certain various embodiments, the face plate member engaging surface 20 has a lengthwise axis L and a crosswise axis C in which the crosswise axis C is less than the lengthwise axis L. As depicted, the lengthwise axis L is oriented parallel to a radial axis R through the tubing T when the connector 12 of the device 10 is in position relative to the stethoscope or other medical device. In certain embodiments, it is contemplated the lengthwise axis L will be no more than 25% greater than the crosswise axis C.

The connector 12 of the device 10 also has a tubing engaging region 22 opposed to the face plate member engaging surface 20. The tubing engaging region 22 is configured with at least two arms 24, 24' and can be positioned proximate to a central region 28.

The central region 28 can be configured with suitable ridges or bulges configured to assist in engagement and retention of the face plate member 14 where desired or required. The central surface 26 will generally be positioned at a location opposed to the face plate member engaging surface 20 at a spaced distance thereto. This distance will generally define the height of the central region 28 with its other dimensions having a value greater than or equal to the dimensions defined by the face plate member engagement region.

In various embodiments, the connector 12 will have a height H with the tubing engaging region 22, each having a height $H_a$ in which the height $H_a$ is at least 50% of the value of the height H. In certain applications, the height of the arms The connector 12 has a first side face 30 and an opposed second side face 30'. The first and second side faces 30, 30' are contiguously connected to the face plate member engaging surface and extending angularly outward therefrom to define an interior angle less than 180° with angles of approximately 90° being typical in certain applications. The central region 28 and interior surfaces of the arms 24, 24' extend from the first side face 30 to the opposed second side face 30'. In the embodiments depicted, the first and second side faces 30, 30' are planar and are disposed parallel to one another.

The connector 12 also includes a first lateral surface 32 and an opposed lateral surface 32'. The first and second lateral surfaces 32, 32' are connected to the face plate member engaging surface 20. In the embodiments depicted, the first and second lateral surfaces 32, 32' are contiguously connected to surface 20. The first and second lateral surfaces 32, 32' extend angularly outward therefrom to define an interior angle less than 180° with angles of approximately 90° being typical in certain applications. The first and second lateral surfaces 32, 32' extend between associated outer edges of the side walls of the first and second side faces 30, 30'.

The embodiment depicted in the device 10 has two arms 24, 24' projecting outwardly in a direction opposed to the face plate member engaging surface 20. The arms 24, 24' are in spaced relationship to one another and are connected to one another by a central surface 26. The arms 24, 24' and central surface 26 define a tubing-receiving region 31 configured to receive a section of the tubing T in friction fit engagement thereto.

The arms 24, 24' can be disposed parallel to one another through their respective lengths and can project outward to a length generally greater than 50% of the diameter of the tubing of the medical device to which the device 10 is to be attached. In the embodiment depicted in the various drawing figures, the arms 24, 24' project outward to a length that permits extension to a point that equals at least 75% of the diameter of the tube with 90% of the diameter being contemplated in some instances.

In various embodiments, the tubing-receiving region 31 will have a width between 95% and 100% of the diameter associated tubing T and about 60% and 100% of the diameter of the associated tubing T, with lengths between 75% and 95% of the diameter in certain applications.

The arms 24, 24' have an interior surface regions of the first and second lateral surfaces 32, 32' that are contiguous to the central region 28 disposed in spaced parallel relationship to one another at a outer distance having a value of $W_a$, when viewed at a cross section parallel to the crosswise axis C.

The connector 12 of the device 10 also includes the central region 28 interposed between the face plate member engaging surface 20 and the tubing engaging region 22. The central region 28 has a pair of opposed protrusions 34, 34' when viewed in a cross section taken along a line parallel to the crosswise axis C. The pair of opposed protrusions 34, 34' are curved regions that project to a maximum width W such that the width W is greater than a width $W_a$. The pair of opposed protrusions 34, 34' will have a size suitable to stabilize and orient the connector 12 relative to the associated tubing T to which it is attached. In certain embodiments, it is contemplated that the width W will be between 10 and 25% greater than the width $W_a$.

Figure 2A:
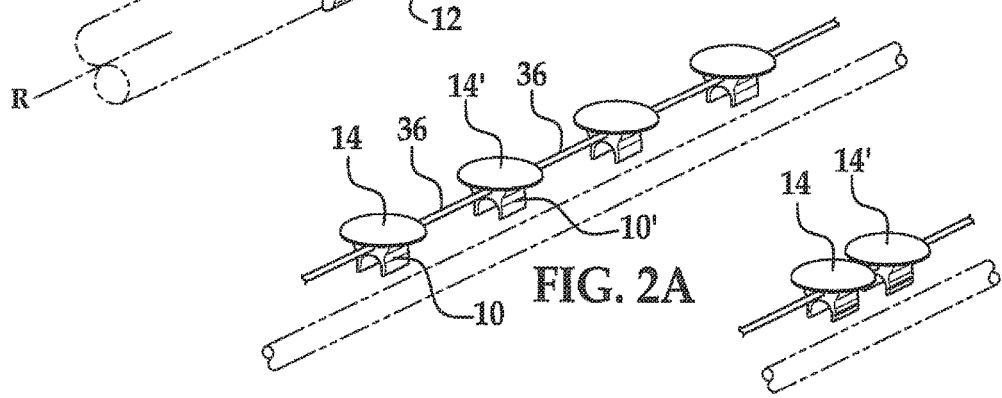
FIG. 2A is an alternative embodiment of the decorative face plate member of FIG. 2.
Figure 2B:
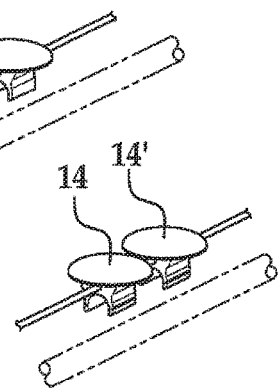
FIG. 2B is an alternative embodiment of the decorative face plate member of FIG. 2.

The central region 28 and the associated pair of opposed protrusions 34, 34' will be defined by the same height Ha, with the connector height H being the sum of $H_a + H_b$ and the maximum height of the interior tube-receiving region 31 being equal to $H_b$.

Where desired or required, the device 10 can be employed in combination with an additional devices 10' as depicted in FIGS. 2A and 2B. The various devices can have interlocking decorative face plate members 14, 14' as depicted in FIG. 2B. The various devices 10, 10' etc. can be spaced apart on the tubing T as depicted in FIG. 2A and can be joined by suitable decorative threads, chains etc. as at reference numeral 36.

Where desired or required, the device 10 can also be equipped with at suitable tracking or signalling device to assist in locating the associated medical instrument if it is lost or mislaid. Non-limiting examples of such locational aid includes various radio frequency devices and the like.

The device 10 can be located on and removably attached to a tubing portion of a suitable device such as a stethoscope. Where it is employed, one or more devices 10 are attached at suitable locations on the stethoscope S such as on an upper tubing 40 proximate to an ear piece 42 and a lower tubing 45 between a junction 44 and a chest piece 46. The attachment of the respective devices 10 may cause a minor deformation of the flexible material employed in the tubing T. However the degree of deformation is insufficient to impair functioning of the lumen or lumens housed within the tubing T.

The respective arms 24, 24' have leading surface regions 48, 48' contoured to facilitate attachment to the associated tubing T. In the embodiment depicted in the various drawing figures, the leading surface regions 48, 48' are each configured with angular inner edge and a quarter round outer contour. The quarter round outer contour is configured to echo the associated dimension of the tubing T.

The device 10 configured with the arms 24, 24' can be attached to the associated tubing by exerting pressure in the connector 12 in a plane essentially perpendicular to the radial axis R of the tubing T. The action results in a slight deformation of the tubing T in the region of attachment. The deformative pressure is sufficient to keep the connector 12 in place on the tubing T. Thus the attachment mechanism employed can be a combination of mechanical and friction fit.

The device 10 is configured such that the decorative face plate member 14 can be attached to the connector 12 either before or after attachment to the tubing T depending upon considerations including but not limited to the configuration and/or deformative nature of the respective face plate member 14. The device 10 can be removed from association with the respective medical instrument S when desired or required by reversing the attachment process. The connector 12 can be grasped or urged from engagement by suitable manual pressure. The decorative face plate member 14 can be removed prior to removal of the connector 12. However in certain situations, it is contemplated that the two members will be removed in one action.

The connector 12 and decorative face plate member 14 can be made of any suitable material. It is contemplated that the material(s) of choice will be those that can withstand typical usage with the associated instrument. Where sterilization and/or autoclaving of the associated instrument are likely, it is contemplated that the material(s) will be one(s) that can withstand the associated cleaning and sanitizing methods. In various embodiments suitable metals, including but not limited to surgical steel can be employed. It is also contemplated that the connector 12 may be composed of a suitable metal such as surgical steel and the decorative face plate member 14 can be composed of a different, possible more ornamental material.

The device(s) 10 can be oriented on the tubing T of the associated medical device in any manner desired by the wearer/user. The decorative face plate members 14, 14' can be oriented in any suitable manner relative to the "front" or "back" face of the medical device. In the embodiment depicted in FIG. 3, various devices 10 are oriented at different outward facing angles relative to the device 10. This can be done to permit and facilitate display during use or transit. In situations where the associated medical device is a stethoscope, the medical device may not have a fixed front face. The biaurals can be used in either ear and the medical device may be draped around the neck with biaruals and chest piece hanging over the shoulders at various points during the day. Thus the ability to orient various devices 10 provides decorative flexibility in personalizing the stethoscope or other medical device.

The nature and type of decoration can vary from end use application to end use application. Non-limiting examples of such decorations can include insignia from the user's educational institution(s), various affinity groups, cheerful and/or conversational charms, promotional or educational prompts, as well as various aesthetic or artistic elements desired by the user.

It is also contemplated that the device 10 disclosed herein can be used as "rewards" for patients in various long term institutional settings such as cancer clinics and the like. It is envisioned that the device 10 can be configured as "charms" in shaped and features desired by a young patient. These can be carried on the stethoscope of the medical practitioner and transferred to a suitable tubular bracelet, amulet or the like carried or worn by the paediatric patient upon completion of a difficult or unpleasant procedure or medical visit. Such "charms" can be employed to mark forward progress during prolonged hospitalizations or extended periods of medical treatment such as chemotherapy and the like, to assist in increasing medical compliance and to forge a bond between the patient and the associated medical team.

In summary, the present disclosure can be considered to include a device for attachment a medical instrument having a tubing structure, the device comprising at least one connector configured to removably couple to the tubing structure on the medical instrument; and at least one face plate member attached to the connector, the face plate member having a connection surface and at least one decorative surface.

This connector in this device can include a face plate member engaging surface and a tubing engaging region opposed to the face plate member engaging surface; and a central region interposed between the face plate member engaging surface and the tubing engaging region. The tubing engaging region can comprise a) at least two arms projecting outward from the central surface in a direction opposed to the face plate member engaging surface, the arms in spaced relation to each other, and b) a central surface located between the outwardly projecting arms, the central surface positioned proximate to the central region.

The connector can have a height (H) and wherein the tubing engaging region has a height $(H_a)$ such that $H_a$ is greater than 50% of the H and can further comprise a first side face and an opposed second side face, the first and second side faces contiguously connected outward therefrom, wherein the central surface located between the at least two respective arms extends from the first side face to the second side face. The first and second side faces of the connector can be disposed parallel to one another.

The connector can further include a first lateral surface and an opposed second lateral surface, the first and second lateral surfaces contiguously connected to the face plate member engaging surface and extending angularly outward therefrom. Where desired, the first and second side faces are each planar and are oriented parallel to one another and wherein the first and second lateral faces each have at least two respective surface regions such that at least one region corresponds to and defines the central region of the device and at least one additional region corresponding to the tubing engaging region.

The region of the side face of the respective side faces corresponding to the tubing engaging region is essentially flat and a distance from side face to side face defines the width W and wherein the region of the side face corresponding to the central region defines an outwardly projecting shoulder and the width from side face to side face defines a maximum $W_c$ such that the $W_c$ is greater than the $W_1$. The difference between the $W_c$ and the $W_1$ can be at least 5% of the $W_1$.

The face plate member engaging surface can be a flat planar surface. Where desired, the face plate member engaging surface can be configured as a rectangle.

Also within the scope of this disclosure is the device as previously outlined further including a stethoscope having a chest piece, binaurals and tubing connecting the chest piece to the binaurals, wherein the connector is releasably attached to the tubing. The connector can include a face plate member engaging surface; a tubing engaging region opposed to the face plate engaging surface; and a central region interposed between the face plate member engaging surface and the tubing engaging region. The tubing engaging region can comprise a) at least two arms projecting outward from the central surface in a direction opposed to the face plate member engaging surface, the arms in spaced relation to each other, and b) a central surface located between the outwardly projecting arms, the central surface positioned proximate to the central region. The connector can have a height (H) such that the tubing engaging region has a height $(H_a)$ in which the height $H_a$ is greater than 50% of the H; and wherein the connector further comprises a first side face and an opposed second side face disposed parallel to one another, the first and second side faces contiguously connected outward therefrom, wherein the central surface located between the at least two respective arms extends from the first side face to the second side face as well as a first lateral surface and an opposed second lateral surface, the first and second lateral surfaces contiguously connected to the face plate member engaging surface and extending angularly outward therefrom, wherein the region of the side face of the respective side faces corresponding to the tubing engaging region is essentially flat and a distance from side face to side face defines the width W and wherein the region of the side face corresponding to the central region defines an outwardly projecting shoulder and the width from side face to side face defines a maximum $W_c$ such that the $W_c$ is greater than the width W.

The present disclosure is also directed to a decorative device for use with a medical instrument having a tubing structure that includes at least one connector configured to removably couple to the tubing structure on the medical instrument, the connector having a face plate member engaging structure configured to attachably engage at least tone decorative face plate member. The connector can include a face plate member engaging surface; a tubing engaging region opposed to the face plate member engaging surface; and a central region interposed between the face plate member engaging surface and the tubing engaging region. The tubing engaging region can include a) at least two arms projecting outward from the central surface in a direction opposed to the face plate member engaging surface, the arms in spaced relation to each other, and b) a central surface located between the outwardly projecting arms, the central surface positioned proximate to the central region. The connector can have a height (H) such that the tubing engaging region has a height $(H_a)$ with the $H_a$ being greater than 50% of the height H. The device can also have the face plate member engaging surface is a flat planar surface. The connector can include a first lateral surface and an opposed second lateral surface, the first and second lateral surfaces contiguously connected to the face plate member engaging surface and extending angularly outward therefrom.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed:

1. A device for attachment to a medical instrument having a tubing structure, the device comprising:
   at least one connector configured to removably couple to the tubing structure on the medical instrument, the connector comprising:

a face plate member engaging region;

a tubing engaging member, the tubing engaging member opposed to the face plate member engaging surface, wherein the tubing engaging region comprises at least two arms projecting outward from the central region in a direction opposed to the face plate member engaging surface; and at least one face plate member attached to the connector, the face plate member having a connection surface and at least one decorative surface, wherein the connector has a height (H) and wherein the tubing engaging region has a height ($H_a$) such that $H_a$ is greater than 50% of the H; and wherein the connector further comprises a first side face and an opposed second side face disposed parallel to one another, the first and second side faces contiguously connected outward therefrom, wherein the central surface located between the at least two respective arms extends from the first side face to the second side face as well as a first lateral surface and an opposed second lateral surface, the first and second lateral surfaces contiguously connected to the face plate member engaging surface and extending angularly outward therefrom, wherein the region of the side face of the respective side faces corresponding to the tubing engaging region is essentially flat and a distance from side face to side face defines a width $W_1$ and wherein the region of the side face corresponding to the central region defines an outwardly projecting shoulder and the width from side face to side face defines a maximum $W_c$ such that $W_c$ is greater than $W_1$.

2. A medical instrument having a tubing structure, the medical instrument comprising at least one decorative member, the decorative member comprising:

at least one connector configured to removably couple to the tubing structure on the medical instrument, the connector having a face plate member engaging structure configured to attachably engage at least one decorative face plate member; and at least one face plate member attached to the connector, the face plate member having a connection surface and at least one convex decorative surface;

wherein the medical instrument is a stethoscope having a chest piece, binaurals and tubing connecting the chest piece to the binaurals, wherein the connector is releasably attached to the tubing and the tubing has an external surface, wherein the at least one member is connected to either the chest piece or a binaural and wherein the connector comprises:

a face plate member engaging surface;

a tubing engaging region opposed to the face plate member engaging surface; and a central region interposed between the face plate member engaging surface and the tubing engaging region.

3. The device of claim 2 wherein the tubing engaging region comprises:

a) at least two arms projecting outward from the central region in a direction opposed to the face plate member engaging surface, the arms in spaced relation to each other; and b) a central surface located between the outwardly projecting arms, the central surface positioned proximate to the central region.

4. The device of claim 3 wherein the connector further comprises a first lateral surface and an opposed second lateral surface, the first and second lateral surfaces contiguously connected to the face plate member engaging surface and extending angularly outward therefrom.

5. The device of claim 2 wherein the connector has a height (H) and wherein the tubing engaging region has a height ($H_a$) such that $H_a$ is greater than 50% of the H.

6. The device of claim 2 wherein the face plate member engaging is a flat planar surface.

7. The device of claim 2 comprising at least two members, wherein at least one of the members is connected on a binaural and at least one member is connected to the chest piece.

8. The device of claim 2 comprising at least two members, wherein at least one of the members is connected on a first binaural and at least one member is connected on a second binaural.

* * * * *